United States Patent [19]
Reiffenrath et al.

[11] Patent Number: 5,560,863
[45] Date of Patent: Oct. 1, 1996

[54] 2-FLUOROCYCLOHEXENE DERIVATIVES

[75] Inventors: Volker Reiffenrath, Rossdorf; Herbert Plach, Darmstadt, both of Germany

[73] Assignee: Merck Patent Gesellschaft Mit Beschrankter Haftung, Darmstadt, Germany

[21] Appl. No.: 411,652

[22] PCT Filed: Aug. 1, 1994

[86] PCT No.: PCT/EP94/02546

§ 371 Date: Apr. 5, 1995

§ 102(e) Date: Apr. 5, 1995

[87] PCT Pub. No.: WO95/04790

PCT Pub. Date: Feb. 16, 1995

[30] Foreign Application Priority Data

Aug. 6, 1993 [DE] Germany .................. 43 26 420.4

[51] Int. Cl.$^6$ .................. C09K 19/52; C09K 19/34; C09K 19/30; G02F 1/13; C07C 23/10
[52] U.S. Cl. .................. 252/299.01; 252/299.61; 252/299.63; 252/299.62; 252/299.66; 359/103; 570/131
[58] Field of Search .................. 252/299.01, 299.61, 252/299.62, 299.63, 299.66; 359/103; 570/127, 131

[56] References Cited

U.S. PATENT DOCUMENTS

| | | | |
|---|---|---|---|
| 4,846,998 | 7/1989 | Pohl et al. | 252/299.63 |
| 5,356,560 | 10/1994 | Reiffenrath et al. | 252/299.61 |

FOREIGN PATENT DOCUMENTS

| | | |
|---|---|---|
| 4035509 | 5/1992 | Germany . |
| 4227772 | 2/1994 | Germany . |
| 5310616 | 1/1993 | Japan . |

*Primary Examiner*—Shean C. Wu
*Attorney, Agent, or Firm*—Millen, White, Zelano & Branigan, P. C.

[57] ABSTRACT

2-Fluorocyclohexene derivatives of formula I

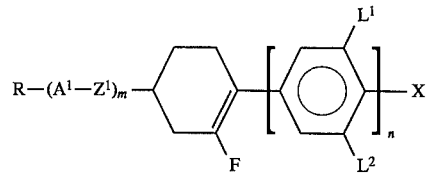

where

R, $A^1$, $Z^1$, X, $L^1$, $L^2$, m and n are as defined herein, and their use as components of liquid-crystalline media for electro-optical display elements, in particular for matrix liquid-crystal displays.

12 Claims, No Drawings

2-FLUOROCYCLOHEXENE DERIVATIVES

This application is a 371 of PCT/EP94/02546 filed Aug. 1, 1994.

The present invention relates to 2-fluorocyclohexene derivatives of the formula I

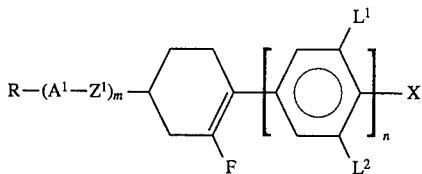

where

R is an alkyl or alkenyl radical having up to 18 carbon atoms which is unsubstituted or substituted by CN or by at least one halogen and in which one or more non-adjacent $CH_2$ groups can be replaced by a radical selected from the group consisting of —O—, —S—, —CO—, —O—CO—, —CO—O— and —C≡C—, $A^1$
 a) is a 1,4-phenylene radical, in which one or two CH groups can be replaced by N,
 b) is a 1,4-cyclohexylene radical, in which one or two non-adjacent $CH_2$ groups can be replaced by —O— or —S—,
 c) is a 1,4-cyclohexenylene, piperidine-1,4-diyl, 1,4-bicyclo[2.2.2]octylene or naphthalene-2,6-diyl radical, where the radicals a) and b) can be monosubstituted or polysubstituted by halogen atoms or cyano and/or methyl groups, $Z^1$ is —$CH_2CH_2$—, —CO—O—, —O—CO—, —CH=CH—, —$OCH_2$—, —$CH_2O$—, —C≡C—, —$(CH_2)_4$—, —CH=CH—$CH_2CH_2$— or a single bond, X is alkyl or alkoxy having 1 to 12 carbon atoms, NCS or Q—Y, where Q is —O—, —S— or a single bond, and Y is CN, F, Cl or halogenated alkyl or alkenyl having 1 to 5 carbon atoms, $L^1$ and $L^2$ are each, independently of one another, H or F, m is 0, 1 or 2, and n is 0, 1 or 2, where m+n≧1, with the proviso that, in the case where m=1, n=0 and X=alkyl, alkoxy, F, Cl or CN, $L^1$ and $L^2$ are fluorine.

The invention furthermore relates to the use of these compounds as components of liquid-crystalline media and to liquid-crystal and electro-optical display elements containing the liquid-crystalline media according to the invention.

The compounds of the formula I can be used as components of liquid-crystalline media, in particular for displays based on the principle of the twisted cell, including highly twisted variants thereof, such as, for example, STN or SBE, the guest-host effect, the effect of deformation of aligned phases or the effect of dynamic scattering, in particular from matrix liquid-crystal displays (MLC displays).

The invention had the object of finding novel, stable, liquid-crystalline or mesogenic compounds which are suitable as components of liquid-crystalline media and in particular have comparatively low viscosity and high positive dielectric anisotropy.

Compounds of the formula

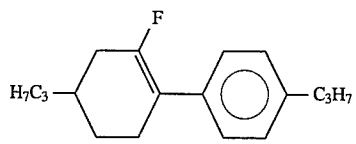

are disclosed in J0 5310616.

It has now been found that compounds of the formula I are eminently suitable as components of liquid-crystalline phases. In particular, they have comparatively low viscosities. They can be used to obtain stable liquid-crystalline phases having a broad mesophase range advantageous values for the optical and dielectric anisotropy, which are at the same time distinguished by very favorable values for the resistivity. Significant advantages can thus be achieved, in particular in the case of media for matrix liquid-crystal displays (MLC displays) or Supertwist displays.

In addition, the provision of compounds of the formula I very generally considerably broadens the range of liquid-crystalline substances which are suitable, from various application points of view, for the preparation of liquid-crystalline mixtures.

The compounds of the formula I have a broad range of applications. Depending on the chosen substituents, these compounds can be used as base materials from which liquid-crystalline phases are predominantly composed; however, it is also possible to add compounds of the formula I to liquid-crystalline base materials from other classes of compound in order, for example, to modify the dielectric and/or optical anisotropy of the dielectric of this type and/or to optimize its threshold voltage and/or its viscosity and/or resistivity.

In the pure state, the compounds of the formula I are colorless and form liquid-crystalline mesophases in a temperature range which is favorably located for electro-optical use. They are stable chemically, thermally and to light.

The invention thus relates to the compounds of the formula I, in particular the compounds of the formula I in which n+m=2 and/or $L^1$ and $L^2$ are F.

The invention furthermore relates to the use of these compounds as components of liquid-crystalline media.

The invention furthermore relates to liquid-crystalline media containing at least one compound of the formula I and to liquid-crystal display elements, in particular electro-optical display elements, in particular matrix liquid-crystal displays, containing media of this type.

For reasons of simplicity, $A^2$ below denotes

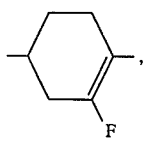

Cyc denotes a 1,4-cyclohexylene or 1,4-cyclohexenylene radical, Dio denotes a 1,3-dioxane-2,5-diyl radical, Dit denotes a 1,3-dithiane-2,5-diyl radical, Phe denotes a 1,4-phenylene radical, Pyd denotes a pyridine-2,5-diyl radical, Pyr denotes a pyrimidine-2,5-diyl radical and Bi denotes a bicyclo(2,2,2)octylene radical, where Cyc and/or Phe can be unsubstituted or monosubstituted or disubstituted by F or CN.

Accordingly, the compounds of the formula I include bicyclic or tricyclic compounds of the sub-formulae Ia to Ip:

R—$A^2$—Phe—X          Ia

R—Cyc—A²—Phe—X      Ib
R—Phe—A²—Phe—X      Ic
R—Dio—A²—Phe—X      Id
R—Dit—A²—Phe—X      Ie
R—Pyd—A²—Phe—X      If
R—Pyr—A²—Phe—X      Ig
R—Bi—A²—Phe—X       Ih
R—A²—Phe—Phe—X      Ii
R—Phe—Z¹—A²—Phe—X   Ij
R—Cyc—Z¹—A²—Phe—X   Ik
R—Dio—Z¹—A²—Phe—X   Il
R—Dit—Z¹—A²—Phe—X   Im
R—Pyd—Z¹—A²—Phe—X   In
R—Pyr—Z¹—A²—Phe—X   Io
R—Bi—Z¹—A²—Phe—X    Ip tetracyclic compounds of the sub-formulae Iq–Iu:

R—A¹—A¹—A²—Phe—X           Iq
R—A¹—Z¹—A¹—A²—Phe—X        Ir
R—A¹—Z¹—A¹—Z¹—A²—Phe—X     Is
R—A¹—A²—Phe—Phe—X          It
R—A¹—Z¹—A²—Phe—Phe—X       Iu

In the compounds of the sub-formulae Ia to Iu which contain one or more bridges Z¹, the bridging members are preferably —CH₂CH₂—, —CO—O—, —O—CO—, —CH₂O—, —OCH₂— or —C≡C—, in particular —CH₂CH₂—.

R is preferably a straight-chain alkyl, furthermore alkoxy and alkenyl.

The compounds of the formula I preferably contain not more than one of the radicals Bi, Pyd, Pyr, Dio or Dit.

Particularly preferred compounds are the fluorocyclohexene derivatives of the formulae I1 to I39:

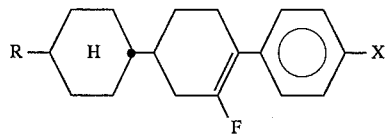  I1

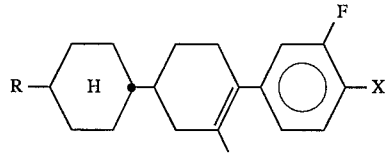  I2

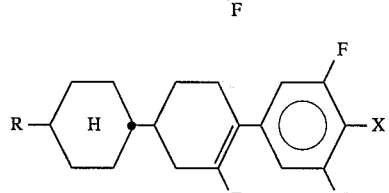  I3

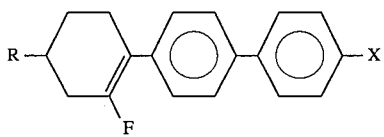  I4

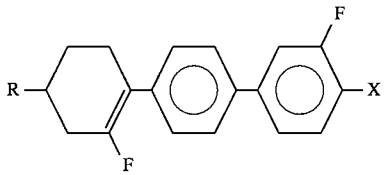  I5

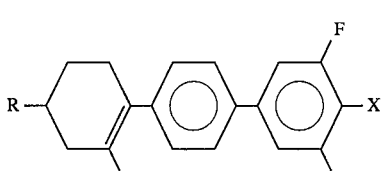  I6

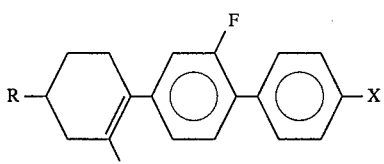  I7

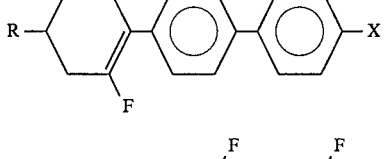  I8

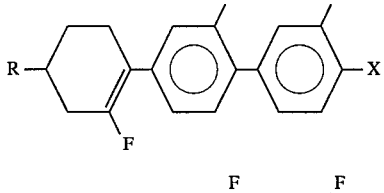  I9

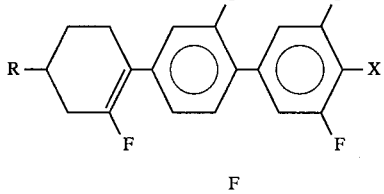  I10

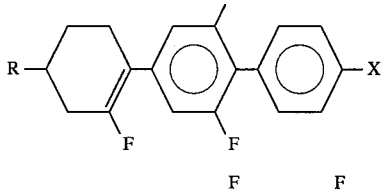  I11

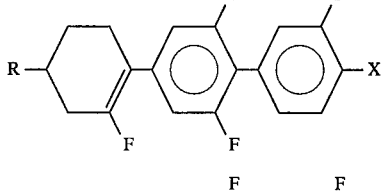  I12

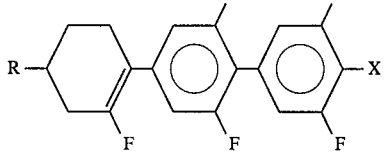

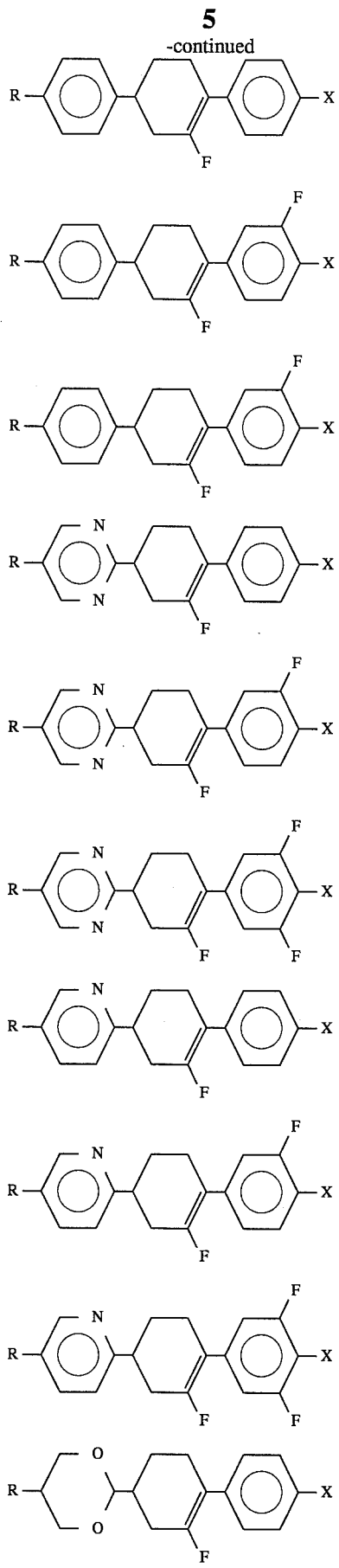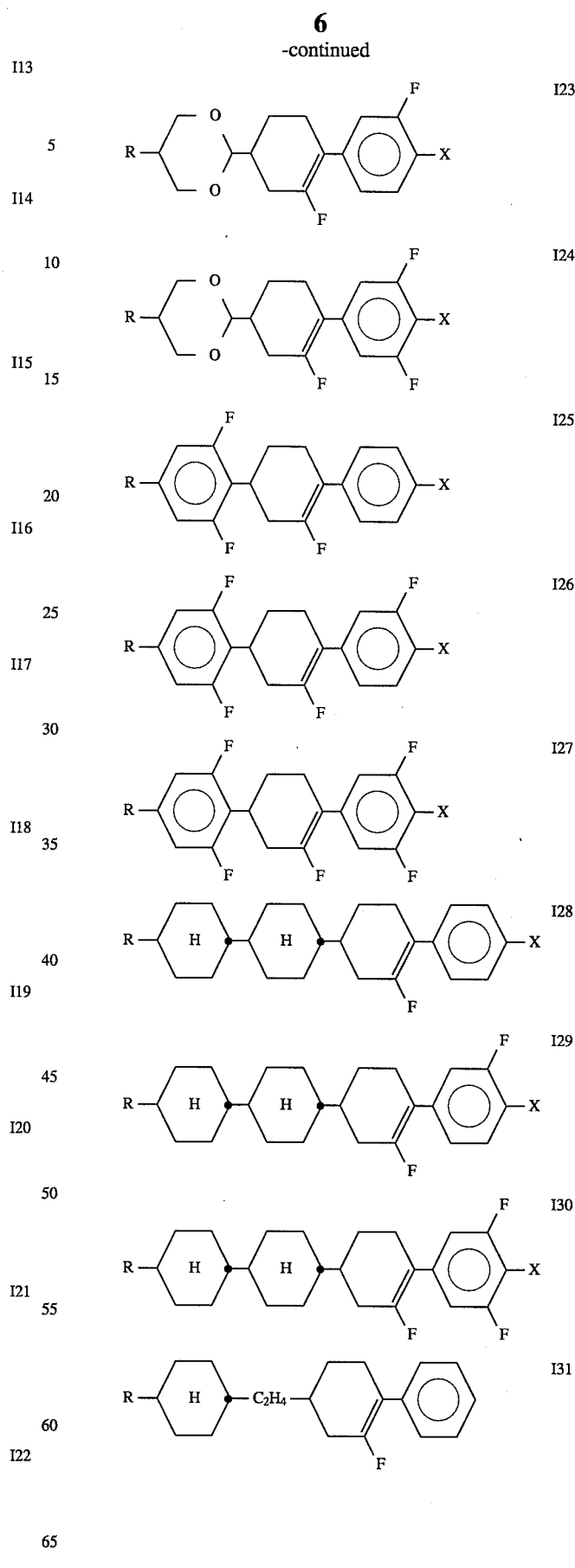

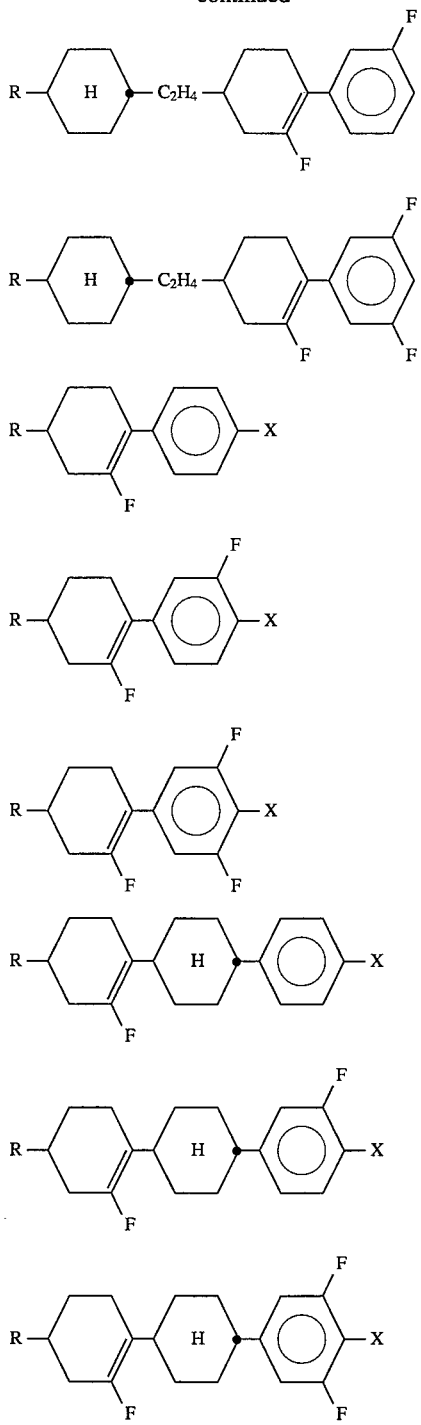

In the compounds of the formula I, X is preferably CN, NCS, OCN, F, Cl, CF$_3$, OCF$_3$, CF$_2$H, CHF$_2$, CF$_2$Cl, OCF$_2$H, OCF$_2$Cl, OCH$_2$CF$_3$, OCHFCF$_3$, OCF$_2$CF$_3$, OCH$_2$CF$_2$H, OCH=CF$_2$, OCF=CF$_2$, OCF=CCl$_2$, OCH$_2$C$_2$Cl, CH$_2$CF$_3$, CH$_2$CF$_2$H, OCF=CH$_2$, CH=CF$_2$, CF=CF$_2$, CF=CH$_2$, OCH$_3$ or C$_2$H$_5$.

Particular preference is given to compounds in which X is F, Cl, CN, OCF$_3$, OCHFCF$_3$, OCHF$_2$, OCH$_2$CF$_3$, OCF=CF$_2$ or OCH=CF$_2$.

Preference is also given to compounds of the formula I in which the 1,4-phenylene rings present in the molecule are monosubstituted or disubstituted by fluorine. These are, in particular, 2-fluoro-1,4-phenylene and 2,6-difluoro-1,4-phenylene.

If R is an alkyl radical or an alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6 or 7-oxaoctyl, 2-, 3-, 5-, 6-, 7- or 8-oxanonyl, or 2-, 3-, 4-, 5-, 6-, 7-, 8 or 9-oxadecyl.

If R is an alkenyl radical, this can be straight-chain or branched. It is preferably straight-chain and has 2 to 10 carbon atoms. Accordingly, it is in particular vinyl, prop-1-, or prop-2-enyl, but-1-, 2- or but-3-enyl, pent- 1-, 2-, 3- or pent-4-enyl, hex-1-, 2-, 3-, 4- or hex-5-enyl, hept-1-, 2-, 3-, 4-, 5-or hept-6-enyl, oct-1-, 2-, 3-, 4-, 5-, 6- or oct-7-enyl, non-1-, 2-, 3-, 4-, 5-, 6-, 7- or non-8-enyl, and dec-1-, 2-, 3-, 4-, 5-, 6-, 7-, 8- or dec-9-enyl.

If R is an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms. Accordingly, they are, in particular, acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-propoxycarbonyl)ethyl, 3-(methoxycarbonyl)propyl, 3-(ethoxycarbonyl)propyl or 4-(methoxycarbonyl)butyl.

If R is an alkenyl radical in which one CH$_2$ group has been replaced by CO or CO—O or O—CO—, this can be straight-chain or branched. It is preferably straight-chain and has 4 to 13 carbon atoms. Accordingly, it is, in particular, acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups R which are suitable for polymerization reactions are suitable for the preparation of liquid-crystalline polymers.

Compounds of the formula I containing branched wing groups R may occasionally be of importance due to better solubility in the conventional liquid-crystalline base materials, but in particular as chiral dopes if they are optically active. Smectic compounds of this type are suitable as components of ferroelectric materials.

Compounds of the formula I having S$_A$ phases are suitable, for example, for thermally addressed displays.

Branched groups of this type generally contain not more than one chain branch. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctaroyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl or 2-methyl-3-oxahexyl.

If R is an alkyl radical in which two or more $CH_2$ groups have been replaced by —O— and/or —CO—O—, this can be straight-chain or branched. It is preferably branched and has 3 to 12 carbon atoms. Accordingly, it is, in particular, biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl 3,3-bis(ethoxycarbonyl)propyl, 4,4-bis(ethoxycarbonyl)butyl, 5,5-bis(ethoxycarbonyl)hexyl.

Compounds of the formula I which contain wing groups R which are suitable for polycondensations are suitable for preparation of liquid-crystalline polycondensates.

The formula I covers the racemates of these compounds and the optical antipodes, and mixtures thereof.

Of these compounds of the formula I and of the sub-formulae, preference is given to those in which at least one of the radicals present therein has one of the preferred meanings given.

In the compounds of the formula I, preferred stereoisomers are those in which the Cyc and piperidine rings are trans-1,4-disubstituted. Those of the abovementioned formulae which contain one or more groups Pyd, Pyr and/or Dio in each case include the two 2,5-positional isomers.

The 1,4-cyclohexenylene group preferably has the following structures:

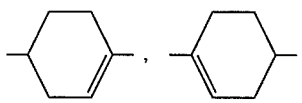

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and are suitable for said reactions. Use can also be made here of variants which are known per se, but are not mentioned here in greater detail.

The fluorocyclohexene derivatives of the formula I according to the invention can be prepared, for example, as follows:

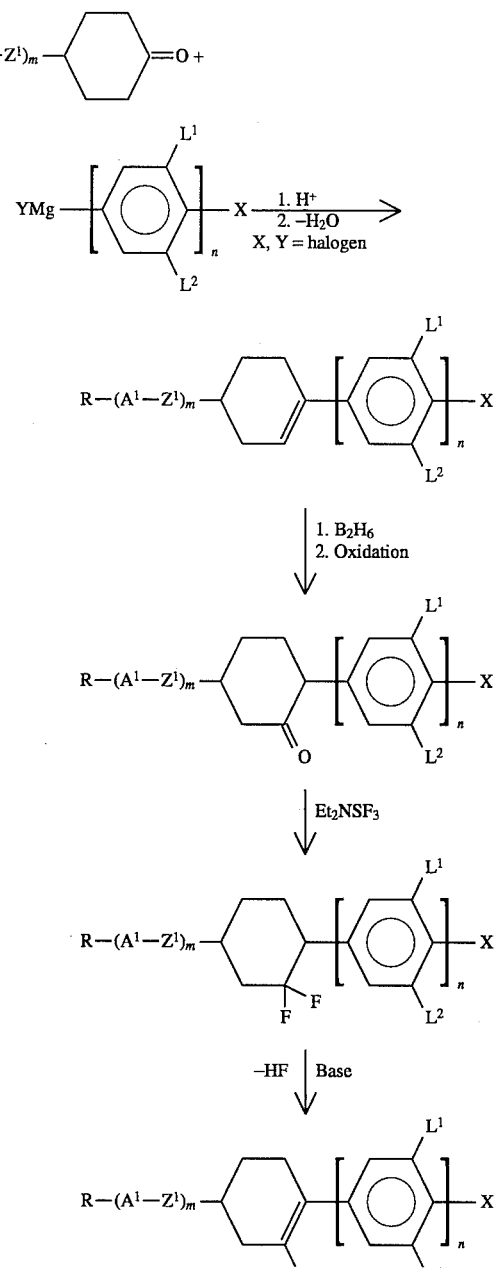

Scheme 2:

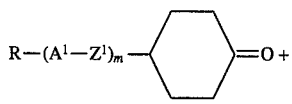

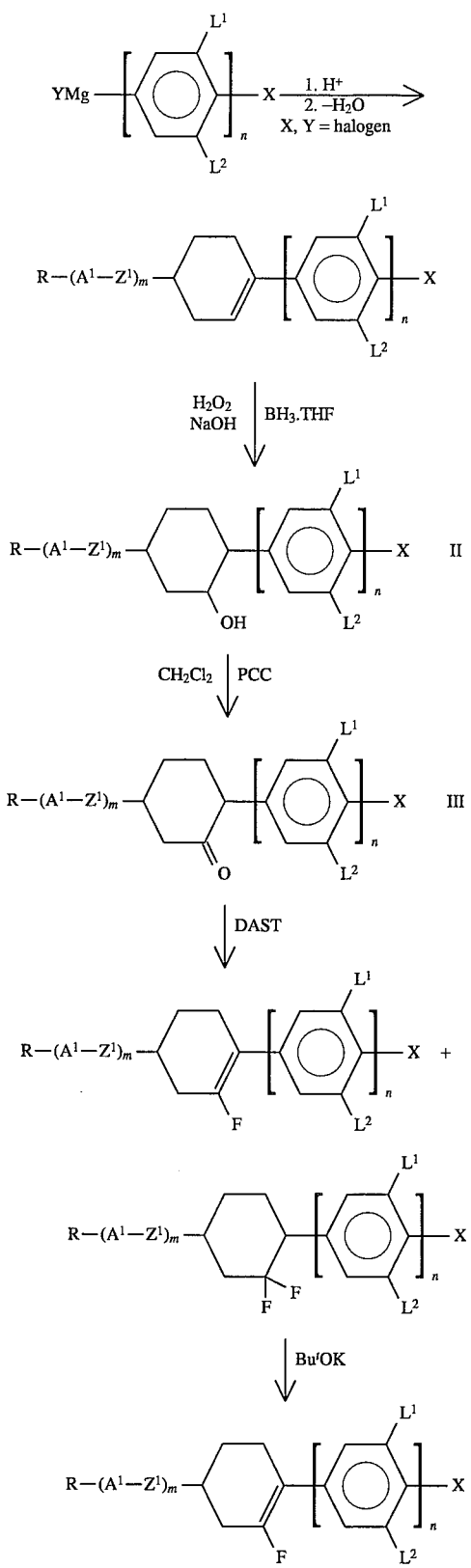
Compounds of the formulae II and III in which R, $A^1$, $Z^1$, $L^1$, $L^2$, X and m are as defined in claim 1, and n is 1 or 2, are likewise a subject-matter of the invention.
The synthesis of some particularly preferred compounds is shown below in greater detail:
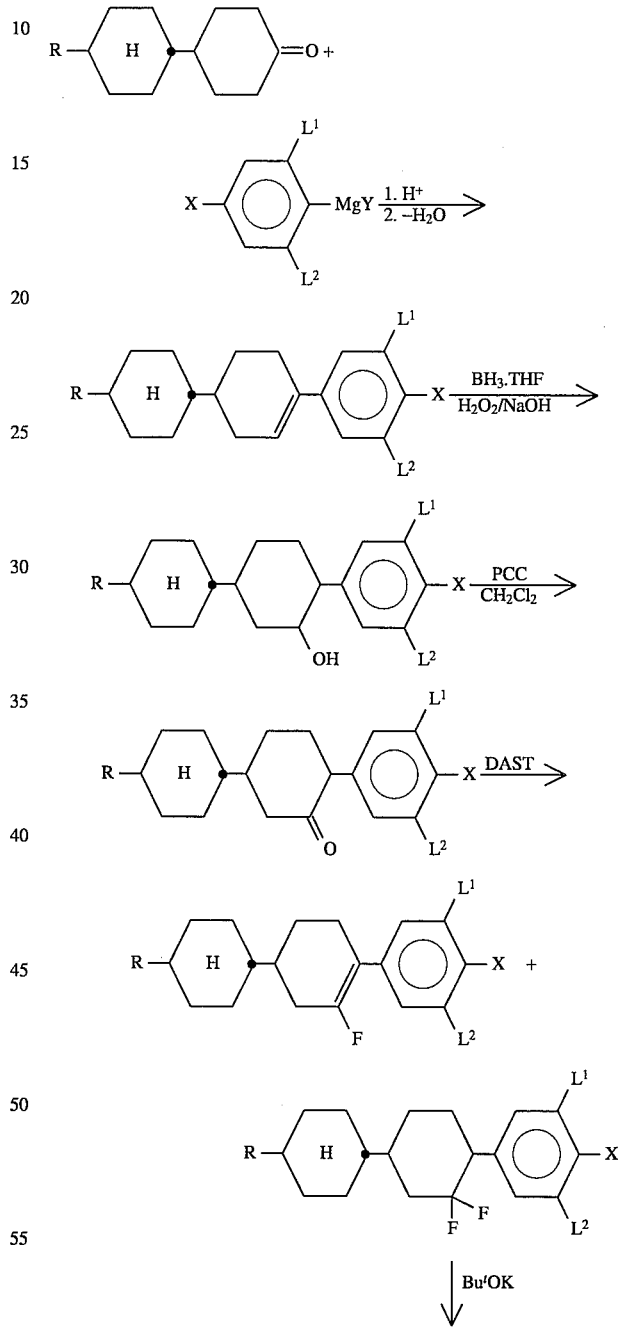

-continued
Scheme 3:

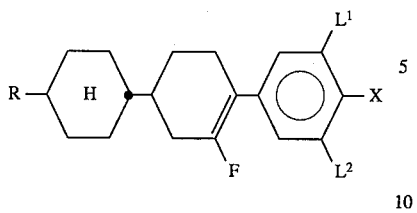

Scheme 4:

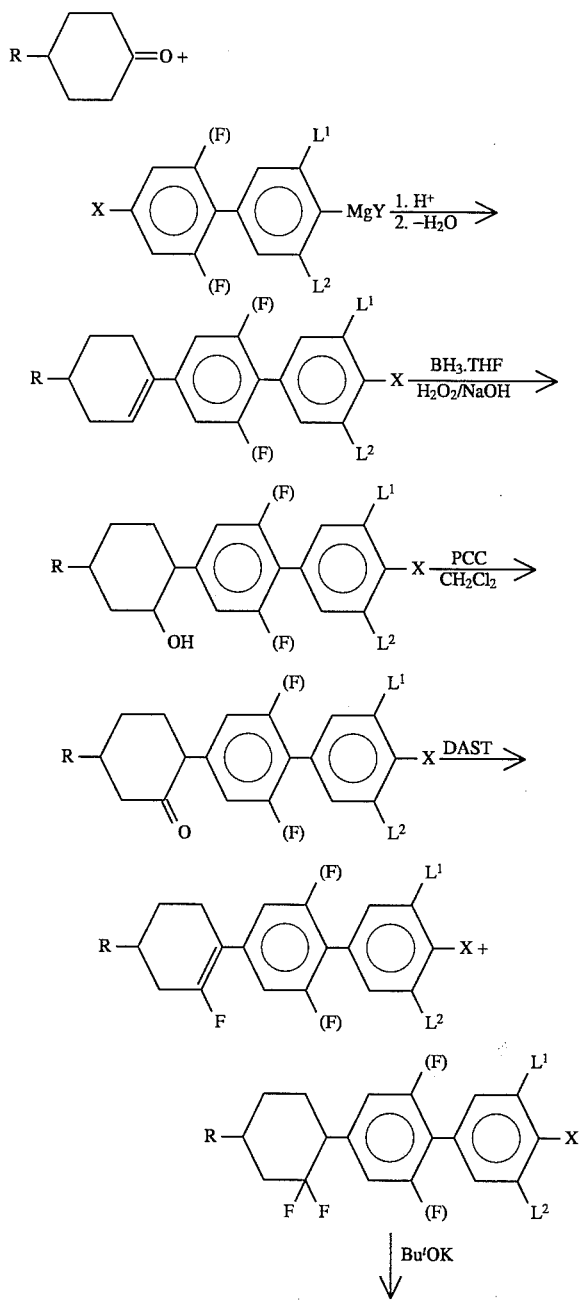

-continued
Scheme 4:

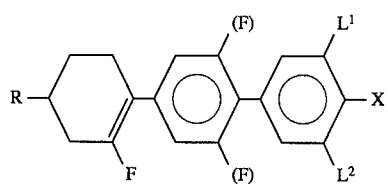

The liquid-crystalline media according to the invention preferably contain 2 to 40, in particular 4 to 30, components as further constituents besides one or more compounds according to the invention. These media very particularly preferably contain 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexyl pyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterized by the formulae 1, 2, 3, 4 and 5:

| | |
|---|---|
| R'—L—E—R" | 1 |
| R'—L—COO—E—R" | 2 |
| R'—L—OOC—E—R" | 3 |
| R'—L—CH$_2$CH$_2$—E—R" | 4 |
| R'—L—C≡C—E—R" | 5 |

In the formulae 1, 2, 3, 4 and 5, L and E, which may be identical or different, are in each case, independently of one another, a bivalent radical from the group formed by —Phe—, —Cyc—, —Phe—Phe—, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,4-diyl and G is 2-(trans-1,4-cyclohexyl)ethyl, pyrimidine-2,5- diyl, pyridine-2,5-diyl or 1,3-dioxane-2,5-diyl.

One of the radicals L and E is preferably Cyc, Phe or Pyr. E is preferably Cyc, Phe or Phe—Cyc. The media according to the invention preferably contain one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group consisting of —Phe—Cyc—, —Cyc—Cyc—, —G—Phe— and —G—Cyc—.

In the compounds of the sub-formulae 1a, 2a, 3a, 4a and 5a, R' and R" are, in each case independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group consisting of the compounds 1a, 2a, 3a, 4a and 5a (Group 1), the media according to the invention preferably also contain components from the group consisting of the compounds 1b, 2b, 3b, 4b and 5b (Group 2), whose proportions are preferably as follows:

Group 1: 20 to 90%, in particular 30 to 90%,

Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of colored guest-host systems, or substances can be added to modify the dielectric anisotropy, the viscosity and/or the orientation of the nematic phases.

The media according to the invention are particularly suitable for use in MLC displays.

In the present application and in the examples below, the structures of the liquid-crystal compounds are indicated by means of acronyms, the transformation into chemical formulae taking place in accordance with Tables A and B below. All radicals $C_nH_{2n+1}$ and $C_mH_{2m+1}$ are straight-chain alkyl radicals having n or m carbon atoms respectively.

The coding in Table B is self-evident. In Table A, only the acronym for the parent structure is given. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+31}$ | F | H | F |
| nF.F.F | $C_nH_{2n+31}$ | F | F | H |
| nCF$_3$ | $C_nH_{2n+31}$ | CF$_3$ | H | H |
| nOCF$_3$ | $C_nH_{2n+31}$ | OCF$_3$ | H | H |
| nOCF$_2$ | $C_nH_{2n+31}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_2H_{2s}$— | CN | H | H |
| nAm | $C_nH_{2n+1}$ | $COOC_mH_{2m+1}$ | H | H |

TABLE A

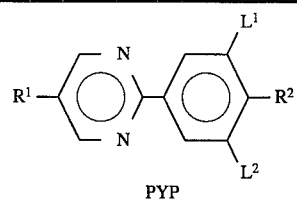

PYP

TABLE A-continued
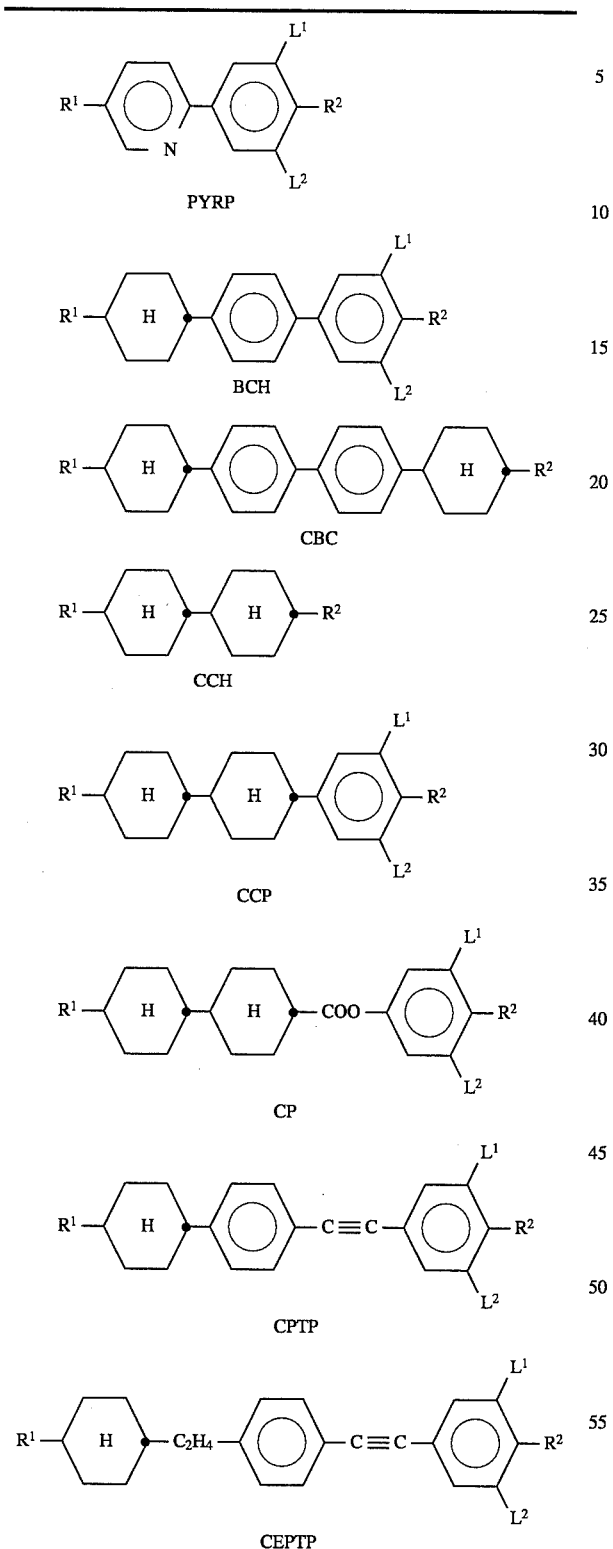
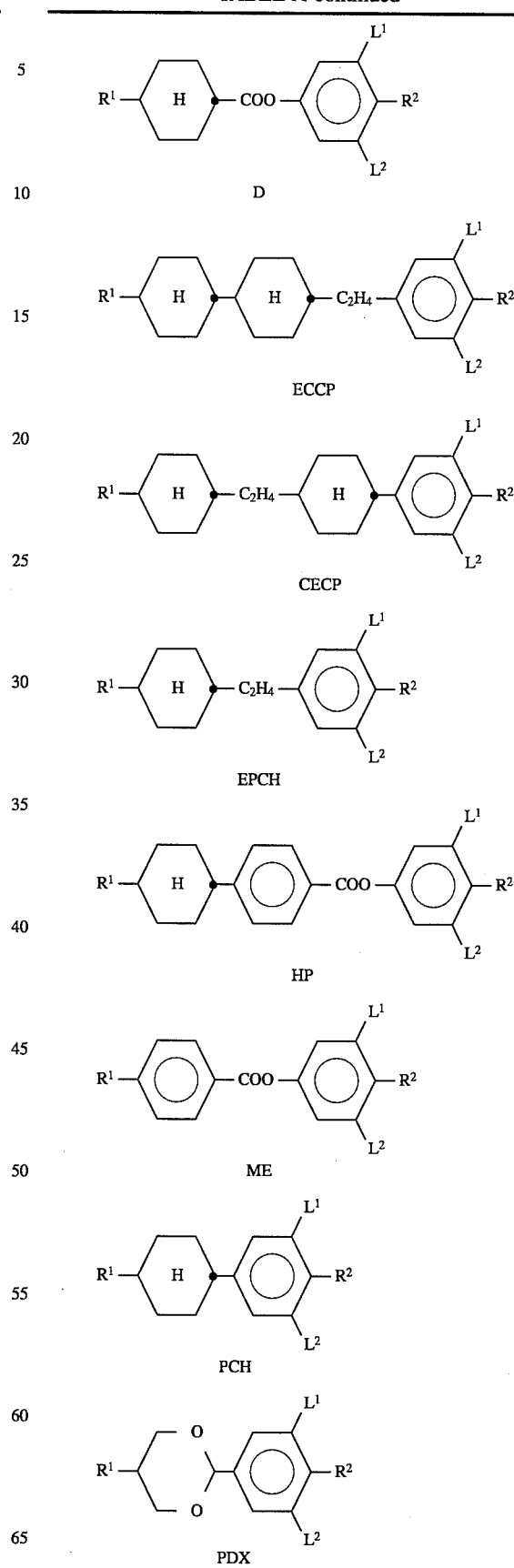

TABLE A-continued
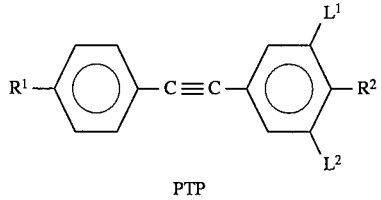
PTP
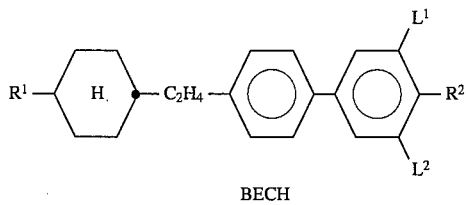
BECH
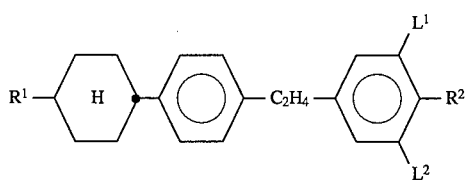
EBCH
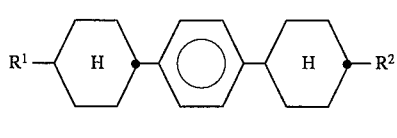
CPC
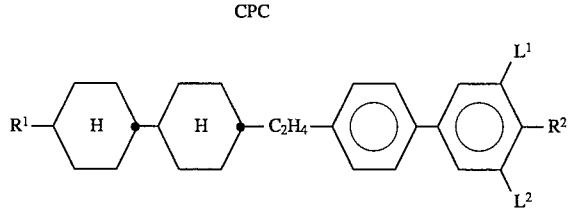
CCEB
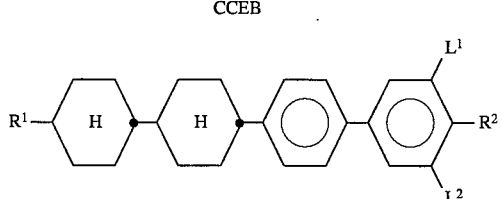
CCB
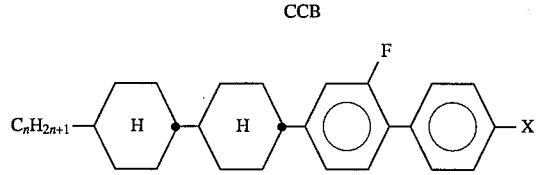
CCB-n.FX
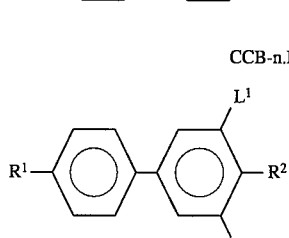
B
TABLE B
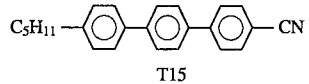
T15
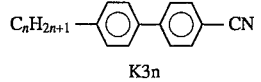
K3n
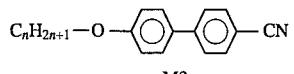
M3n
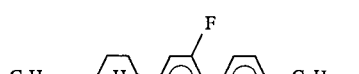
BCH-n.Fm
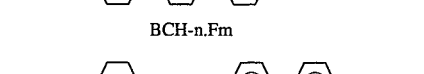
Inm
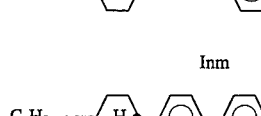
CBC-nmF
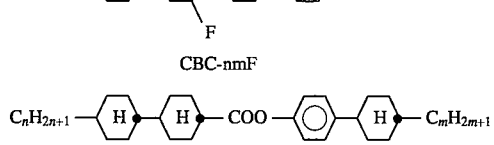
CCPC-nm
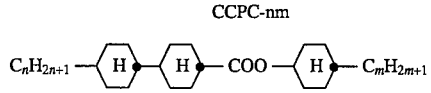
CH-nm
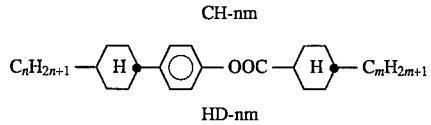
HD-nm
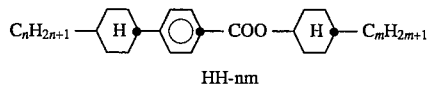
HH-nm
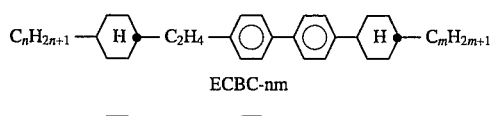
ECBC-nm
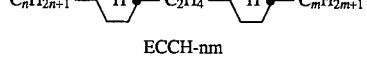
ECCH-nm
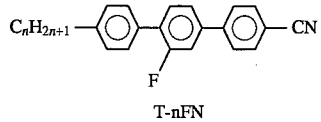
T-nFN
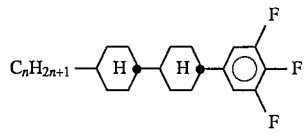
CCP-n.F.F.F

TABLE B-continued

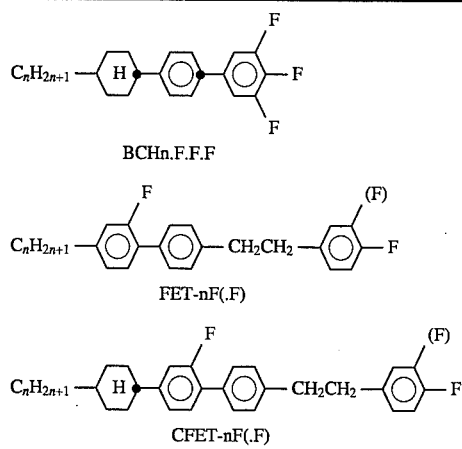

BCHn.F.F.F

FET-nF(.F)

CFET-nF(.F)

The examples below are intended to illustrate the invention without representing a limitation. Above and below, percentages are weight by weight. All temperatures are given in degrees Celsius. m.p.=melting point, c.p.=clearing point. In addition, C=crystalline state, N=nematic state, S=smectic phase and I=isotropic phase. The numbers between these symbols indicate the conversion temperature. An denotes optical anisotropy (589 nm, 20° C.), and the viscosity (mm²/sec) was determined at 20° C.

"Customary work-up" means that water is added, the mixture is extracted with dichloromethane, methyl tertbutyl ether or diethyl ether, the organic phase is separated off, dried and evaporated, and the product is purified by crystallization and/or chromatography.

| DAST | diethylaminosulfur trifluoride |
| DCC | dicyclohexylcarbodiimide |
| DDQ | dichlorodicyanobenzoquinone |
| DIBALH | diisobutylaluminum hydride |
| DMSO | dimethyl sulfoxide |
| POT | potassium tertiary-butoxide |
| THF | tetrahydrofuran |
| pTsOH | p-toluenesulfonic acid |

EXAMPLE 1

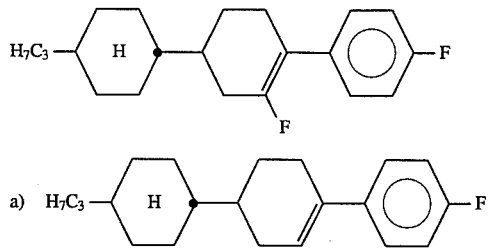

A few drops of bromine are added to a suspension of 1 mol of magnesium turnings in 250 ml of THF. A solution of 1 mol of 1-bromo-4-fluorobenzene in 250 ml of THF is subsequently added dropwise in portions. The mixture is refluxed for 1.5 hours, and 0.9 mol of 4-trans-4-propylcyclohexylcyclohexanone in 500 ml of THF are added dropwise to the Grignard reagent at the boiling temperature. The mixture is refluxed for 1.5 hours, and 1.5 l of water and 200 ml of conc. HCl are added at 30° C. The mixture is stirred for a further ¼ hour, the organic phase is separated off, the aqueous phase is extracted with methyl tert-butyl ether, and the combined organic phases are subjected to customary work-up.

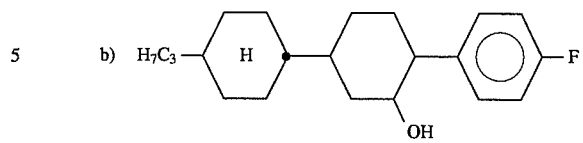

0.2 mol of the cyclohexene derivative from 1a) are dissolved in 500 ml of THF, and 240 ml of $BH_3$. THF complex are added over the course of 0.5 hour at +2° C. The mixture is stirred at +2° C. for a further 1 hour, allowed to warm to room temperature and stirred for a further hour. After addition of 60 ml of ethanol, the mixture is warmed to 30° C., and firstly 40 ml of 6N NaOH and then 80 ml of 30% $H_2O_2$ are added. The mixture is refluxed for 2 hours, allowed to cool to room temperature and hydrolyzed. The aqueous phase is separated off, and the organic phase is diluted with 250 ml of methyl tert-butyl ether. The organic phase is washed with 5% $NaHSO_3$ solution and water and dried over $Na_2SO_4$. The solvent is removed on a Rotavapor, and the residue is recrystallized from n-hexane.

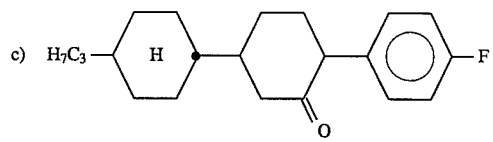

0.094 mol of the cyclohexanol derivative from b) are dissolved in 250 ml of dichloromethane in a nitrogen atmosphere, and 0.14 mol of pyridinium chlorochromate is added. The reaction mixture is refluxed for 2 hours and evaporated. The residue is purified over an $Al_2O_3$/silica gel column.

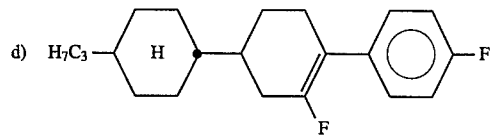

The cyclohexanone derivative (0.02 mol) from c) in 20 ml of dichloromethane is added at room temperature to 0.0382 mol of DAST in 15 ml of dichloromethane. The mixture is refluxed for 4 hours, and the reaction solution is allowed to cool to room temperature overnight. The mixture is hydrolyzed with ice cooling and subsequently subjected to customary work-up:

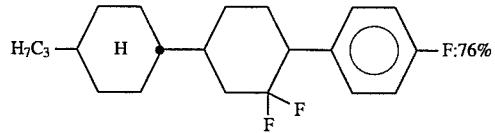

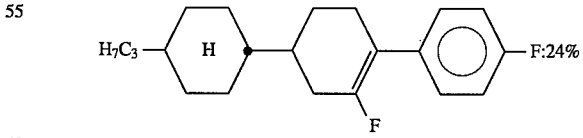

The product (0.01 mol) is, without further purification, dissolved in 50 ml of THF, 0.03 mol of potassium tert-butoxide is added, and the mixture is stirred for 11 hours at 50° C. in an $N_2$ atmosphere. The mixture is allowed to cool to room temperature, ice water and conc. HCl are added, and the mixture is extracted with methyl tert-butyl ether. The product is subsequently subjected to customary work-up. C 40 N 124.5 I; $\Delta n=+0.106$; $\Delta\epsilon=6.76$
The following compounds of the formula
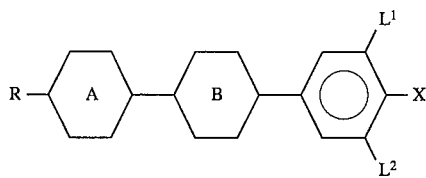
are prepared analogously:
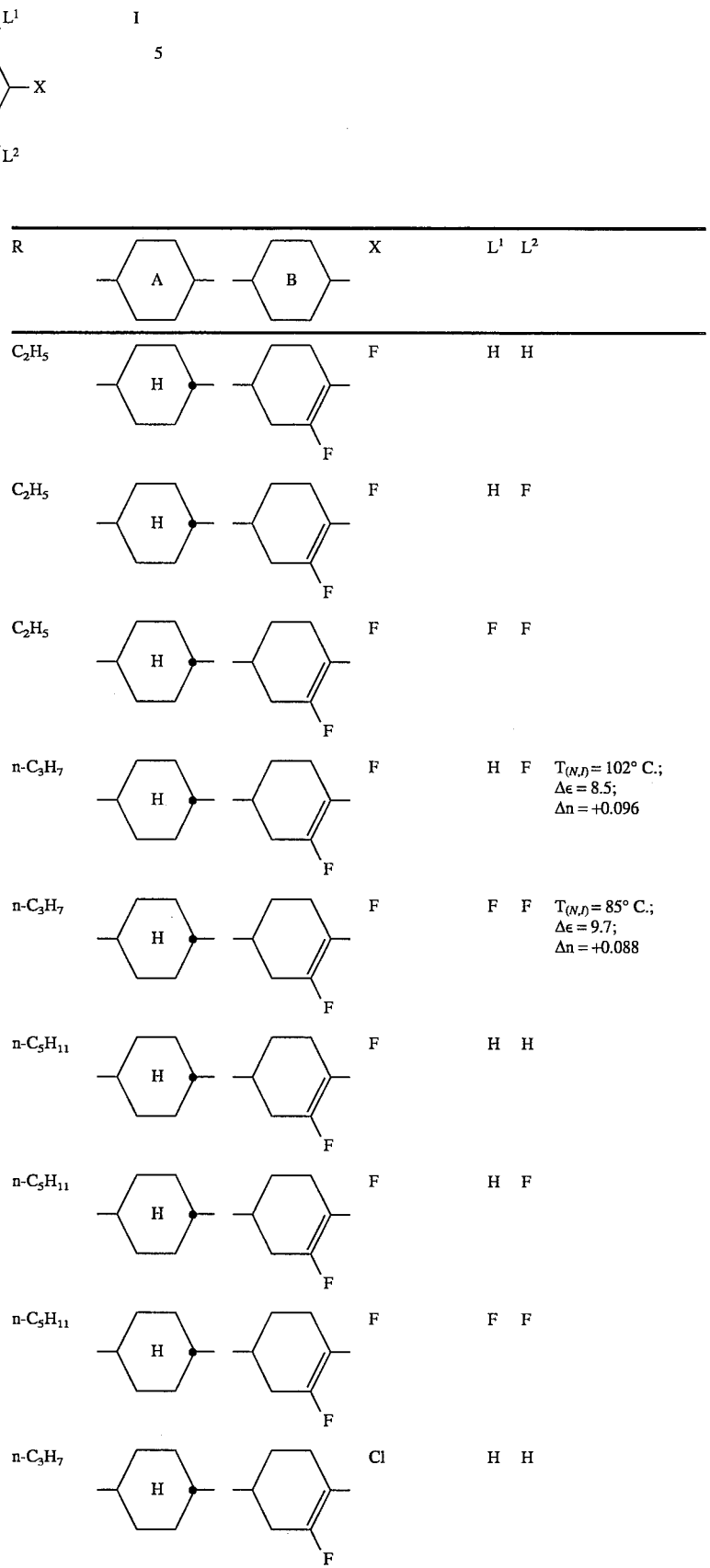

| R | A | B | X | L¹ | L² |
|---|---|---|---|----|----|
| n-C₃H₇ | cyclohexane (H) | cyclohexene-F | Cl | H | F |
| n-C₃H₇ | cyclohexane (H) | cyclohexene-F | Cl | F | F |
| n-C₅H₁₁ | cyclohexane (H) | cyclohexene-F | Cl | H | H |
| n-C₅H₁₁ | cyclohexane (H) | cyclohexene-F | Cl | H | F |
| n-C₅H₁₁ | cyclohexane (H) | cyclohexene-F | Cl | F | F |
| n-C₃H₇ | cyclohexane (H) | cyclohexene-F | CF₃ | H | H |
| n-C₃H₇ | cyclohexane (H) | cyclohexene-F | CF₃ | H | F |
| n-C₃H₇ | cyclohexane (H) | cyclohexene-F | CF₃ | F | F |
| n-C₅H₁₁ | cyclohexane (H) | cyclohexene-F | CF₃ | H | H |
| n-C₅H₁₁ | cyclohexane (H) | cyclohexene-F | CF₃ | H | F |

-continued

| R | A | B | X | L¹ | L² | |
|---|---|---|---|----|----|---|
| n-C₅H₁₁ | H– cyclohexyl | cyclohexenyl-F | CF₃ | F | F | |
| C₂H₅ | H– cyclohexyl | cyclohexenyl-F | OCF₃ | H | H | |
| C₂H₅ | H– cyclohexyl | cyclohexenyl-F | OCF₃ | H | F | |
| C₂H₅ | H– cyclohexyl | cyclohexenyl-F | OCF₃ | F | F | |
| n-C₃H₇ | H– cyclohexyl | cyclohexenyl-F | OCF₃ | H | H | $T_{(N,I)} = 131°$ C.; $\Delta\epsilon = 9.3$; $\Delta n = 0.103$ |
| n-C₃H₇ | H– cyclohexyl | cyclohexenyl-F | OCF₃ | H | F | $T_{(N,I)} = 104°$ C.; $\Delta\epsilon = 11.2$; $\Delta n = +0.093$ |
| n-C₅H₁₁ | H– cyclohexyl | cyclohexenyl-F | OCF₃ | H | H | |
| n-C₅H₁₁ | H– cyclohexyl | cyclohexenyl-F | OCF₃ | H | F | |
| n-C₅H₁₁ | H– cyclohexyl | cyclohexenyl-F | OCF₃ | F | F | |
| C₂H₅ | H– cyclohexyl | cyclohexenyl-F | OCHF₂ | H | H | |

-continued

| R | A-B | X | L¹ | L² | |
|---|---|---|---|---|---|
| $C_2H_5$ | cyclohexyl-H — cyclohexene-F | $OCHF_2$ | H | F | |
| $C_2H_5$ | cyclohexyl-H — cyclohexene-F | $OCHF_2$ | F | F | |
| n-$C_3H_7$ | cyclohexyl-H — cyclohexene-F | $OCHF_2$ | H | H | $T_{(N,I)} = 145°$ C.; $\Delta\epsilon = 7.8$; $\Delta n = +0.086$ |
| n-$C_3H_7$ | cyclohexyl-H — cyclohexene-F | $OCHF_2$ | H | F | $T_{(N,I)} = 126°$ C.; $\Delta\epsilon = 8.9$; $\Delta n = +0.077$ |
| n-$C_3H_7$ | cyclohexyl-H — cyclohexene-F | $OCHF_2$ | F | F | |
| n-$C_5H_{11}$ | cyclohexyl-H — cyclohexene-F | $OCHF_2$ | H | H | |
| n-$C_5H_{11}$ | cyclohexyl-H — cyclohexene-F | $OCHF_2$ | H | F | |
| n-$C_5H_{11}$ | cyclohexyl-H — cyclohexene-F | $OCHF_2$ | F | F | |
| $C_2H_5$ | cyclohexyl-H — cyclohexene-F | $OCH_2CF_3$ | H | H | |
| $C_2H_5$ | cyclohexyl-H — cyclohexene-F | $OCH_2CF_3$ | H | F | |

-continued

| R | A | B | X | L¹ | L² |
|---|---|---|---|----|----|
| $C_2H_5$ | H | F | $OCH_2CF_3$ | F | F |
| $n\text{-}C_3H_7$ | H | F | $OCH_2CF_3$ | H | H |
| $n\text{-}C_3H_7$ | H | F | $OCH_2CF_3$ | H | F |
| $n\text{-}C_3H_7$ | H | F | $OCH_2CF_3$ | F | F |
| $n\text{-}C_5H_{11}$ | H | F | $OCH_2CF_3$ | H | H |
| $n\text{-}C_5H_{11}$ | H | F | $OCH_2CF_3$ | H | F |
| $n\text{-}C_5H_{11}$ | H | F | $OCH_2CF_3$ | F | F |
| $n\text{-}C_3H_7$ | H | F | $OCF_2CF_3$ | H | H |
| $n\text{-}C_3H_7$ | H | F | $OCF_2CF_3$ | H | F |
| $n\text{-}C_3H_7$ | H | F | $OCF_2CF_3$ | F | F |

-continued

| R | A | B | X | L¹ | L² |
|---|---|---|---|---|---|
| n-C₅H₁₁ | H | F | OCF₂CF₃ | H | H |
| n-C₅H₁₁ | H | F | OCF₂CF₃ | H | F |
| n-C₅H₁₁ | H | F | OCF₂CF₃ | F | F |
| n-C₃H₇ | H | F | OCH₂CF₂H | H | H |
| n-C₃H₇ | H | F | OCH₂CF₂H | H | F |
| n-C₃H₇ | H | F | OCH₂CF₂H | F | F |
| n-C₅H₁₁ | H | F | OCH₂CF₂H | H | H |
| n-C₅H₁₁ | H | F | OCH₂CF₂H | H | F |
| n-C₅H₁₁ | H | F | OCH₂CF₂H | F | F |
| C₂H₅ | H | F | OCH=CF₂ | H | H |

-continued

| R | A | B | X | L¹ | L² |
|---|---|---|---|----|----|
| C₂H₅ | H | F (cyclohexene) | OCH=CF₂ | H | F |
| C₂H₅ | H | F (cyclohexene) | OCH=CF₂ | F | F |
| n-C₃H₇ | H | F (cyclohexene) | OCH=CF₂ | H | H |
| n-C₃H₇ | H | F (cyclohexene) | OCH=CF₂ | H | F |
| n-C₃H₇ | H | F (cyclohexene) | OCH=CF₂ | F | F |
| n-C₅H₁₁ | H | F (cyclohexene) | OCH=CF₂ | H | H |
| n-C₅H₁₁ | H | F (cyclohexene) | OCH=CF₂ | H | F |
| n-C₅H₁₁ | H | F (cyclohexene) | OCH=CF₂ | F | F |
| n-C₃H₇ | H | F (cyclohexene) | OCH₂C₂F₅ | H | H |
| n-C₃H₇ | H | F (cyclohexene) | OCH₂C₂F₅ | H | F |

-continued

| R | A | B | X | L¹ | L² | |
|---|---|---|---|----|----|---|
| n-C₃H₇ | H(cyclohexane) | cyclohexene-F | OCH₂C₂F₅ | F | F | |
| n-C₅H₁₁ | H(cyclohexane) | cyclohexene-F | OCHFCF₃ | H | H | |
| n-C₅H₁₁ | H(cyclohexane) | cyclohexene-F | OCHFCF₃ | H | F | |
| n-C₅H₁₁ | H(cyclohexane) | cyclohexene-F | OCHFCF₃ | F | F | |
| n-C₃H₇ | H(cyclohexane) | cyclohexene-F | CN | H | H | $T_{(N,I)} = 203°$ C.; $\Delta\epsilon = 21.0$; $\Delta n = +0.129$ |
| n-C₃H₇ | H(cyclohexane) | cyclohexene-F | CN | H | F | |
| n-C₃H₇ | H(cyclohexane) | cyclohexene-F | CN | F | F | |
| n-C₅H₁₁ | H(cyclohexane) | cyclohexene-F | CN | H | H | |
| n-C₅H₁₁ | H(cyclohexane) | cyclohexene-F | CN | H | F | |
| n-C₅H₁₁ | H(cyclohexane) | cyclohexene-F | CN | F | F | |

-continued

| R | A | B | X | L¹ | L² |
|---|---|---|---|----|----|
| n-C₃H₇ | H | F | C₂H₅ | H | H |
| n-C₃H₇ | H | F | C₂H₅ | H | F |
| n-C₃H₇ | H | F | C₂H₅ | F | F |
| n-C₅H₁₁ | H | F | n-C₃H₇ | H | H |
| n-C₅H₁₁ | H | F | n-C₃H₇ | H | F |
| n-C₅H₁₁ | H | F | n-C₃H₇ | F | F |
| n-C₃H₇ | H | F | OCH₃ | H | H |
| n-C₃H₇ | H | F | OCH₃ | H | F |
| n-C₃H₇ | H | F | OCH₃ | F | F |
| n-C₅H₁₁ | H | F | OC₂H₅ | H | H |

-continued
| R | A | B | X | L¹ | L² |
|---|---|---|---|----|----|
| n-C₅H₁₁ | 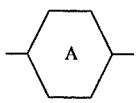 |  | OC₂H₅ | H | F |
| n-C₅H₁₁ | 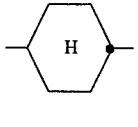 | 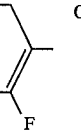 | OC₂H₅ | F | F |
| C₂H₅ | 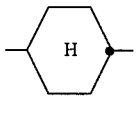 | 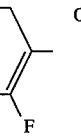 | F | H | H |
| C₂H₅ | 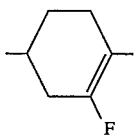 | 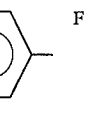 | F | H | F |
| C₂H₅ | 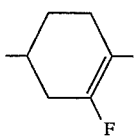 | 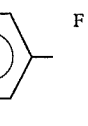 | F | F | F |
| C₂H₅ | 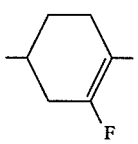 | 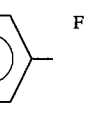 | F | H | H |
| C₂H₅ | 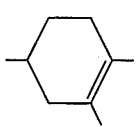 | 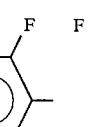 | F | H | F |
| C₂H₅ | 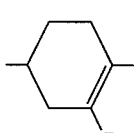 | 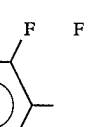 | F | F | F |
| C₂H₅ | 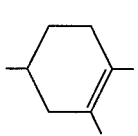 | 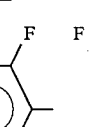 | F | H | H |
| C₂H₅ | 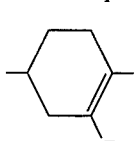 | 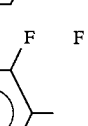 | F | H | F |

-continued

| R | A | B | X | L¹ | L² |
|---|---|---|---|----|----|
| C₂H₅ | cyclohexene-F | phenyl-F,F | F | F | F |
| n-C₃H₇ | cyclohexene-F | phenyl | F | H | H |
| n-C₃H₇ | cyclohexene-F | phenyl | F | H | F |
| n-C₃H₇ | cyclohexene-F | phenyl | F | F | F |
| n-C₃H₇ | cyclohexene-F | phenyl-F | F | H | H |
| n-C₃H₇ | cyclohexene-F | phenyl-F | F | H | F |
| n-C₃H₇ | cyclohexene-F | phenyl-F | F | F | F |
| n-C₃H₇ | cyclohexene-F | phenyl-F,F | F | H | H |
| n-C₃H₇ | cyclohexene-F | phenyl-F,F | F | H | F |

-continued

| R | A—B | X | L¹ | L² | |
|---|---|---|---|---|---|
| n-C₃H₇ | cyclohexene-F / benzene-F,F | F | F | F | |
| n-C₅H₁₁ | cyclohexene-F / benzene | F | H | H | |
| n-C₅H₁₁ | cyclohexene-F / benzene | F | H | F | $T_{(N,I)} = 62°$ C.; $\Delta\epsilon = 11.5$; $\Delta n = +0.119$ |
| n-C₅H₁₁ | cyclohexene-F / benzene | F | F | F | |
| n-C₅H₁₁ | cyclohexene-F / benzene-F,F | F | H | H | |
| n-C₅H₁₁ | cyclohexene-F / benzene-F | F | H | F | |
| n-C₅H₁₁ | cyclohexene-F / benzene-F,F | F | H | H | |
| n-C₅H₁₁ | cyclohexene-F / benzene-F,F | F | H | F | |
| n-C₅H₁₁ | cyclohexene-F / benzene-F,F | F | F | F | |

-continued

| R | A | B | X | L¹ | L² |
|---|---|---|---|----|----|
| n-C₃H₇ | cyclohexene-F | phenyl | Cl | H | H |
| n-C₃H₇ | cyclohexene-F | phenyl | Cl | H | F |
| n-C₃H₇ | cyclohexene-F | phenyl | Cl | F | F |
| n-C₃H₇ | cyclohexene-F | phenyl-F | Cl | H | H |
| n-C₃H₇ | cyclohexene-F | phenyl-F | Cl | H | F |
| n-C₃H₇ | cyclohexene-F | phenyl-F | Cl | F | F |
| n-C₃H₇ | cyclohexene-F | phenyl-2F | Cl | H | H |
| n-C₃H₇ | cyclohexene-F | phenyl-2F | Cl | H | F |
| n-C₃H₇ | cyclohexene-F | phenyl-2F | Cl | F | F |
| n-C₃H₇ | cyclohexene-F | phenyl | CF₃ | H | H |

-continued

| R | A | B | X | L¹ | L² |
|---|---|---|---|---|---|
| n-C₃H₇ | cyclohexene-F | phenyl | CF₃ | H | F |
| n-C₃H₇ | cyclohexene-F | phenyl | CF₃ | F | F |
| n-C₃H₇ | cyclohexene-F | phenyl-F | CF₃ | H | H |
| n-C₃H₇ | cyclohexene-F | phenyl-F | CF₃ | H | F |
| n-C₃H₇ | cyclohexene-F | phenyl-F | CF₃ | F | F |
| n-C₃H₇ | cyclohexene-F | phenyl-F,F | CF₃ | H | H |
| n-C₃H₇ | cyclohexene-F | phenyl-F,F | CF₃ | H | F |
| n-C₃H₇ | cyclohexene-F | phenyl-F,F | CF₃ | F | F |
| n-C₃H₇ | cyclohexene-F | phenyl | OCF₃ | H | H |

-continued

| R | A | B | X | L¹ | L² |
|---|---|---|---|----|----|
| n-C₃H₇ | cyclohexene-F | phenyl | OCF₃ | H | F |
| n-C₃H₇ | cyclohexene-F | phenyl | OCF₃ | F | F |
| n-C₃H₇ | cyclohexene-F | phenyl-F | OCF₃ | H | H |
| n-C₃H₇ | cyclohexene-F | phenyl-F | OCF₃ | H | F |
| n-C₃H₇ | cyclohexene-F | phenyl-F | OCF₃ | F | F |
| n-C₃H₇ | cyclohexene-F | phenyl-F,F | OCF₃ | H | H |
| n-C₃H₇ | cyclohexene-F | phenyl-F,F | OCF₃ | H | F |
| n-C₃H₇ | cyclohexene-F | phenyl-F,F | OCF₃ | F | F |
| n-C₅H₁₁ | cyclohexene-F | phenyl | OCF₃ | H | H |
| n-C₅H₁₁ | cyclohexene-F | phenyl | OCF₃ | H | F |

-continued

| R | A | B | X | L¹ | L² |
|---|---|---|---|----|----|
| n-C₅H₁₁ | cyclohexene-F | phenyl | OCF₃ | F | F |
| n-C₅H₁₁ | cyclohexene-F | phenyl-F | OCF₃ | H | H |
| n-C₅H₁₁ | cyclohexene-F | phenyl-F | OCF₃ | H | F |
| n-C₅H₁₁ | cyclohexene-F | phenyl-F | OCF₃ | F | F |
| n-C₅H₁₁ | cyclohexene-F | phenyl-F,F | OCF₃ | H | H |
| n-C₅H₁₁ | cyclohexene-F | phenyl-F,F | OCF₃ | H | F |
| n-C₅H₁₁ | cyclohexene-F | phenyl-F,F | OCF₃ | F | F |
| n-C₃H₇ | cyclohexene-F | phenyl | OCHF₂ | H | H |
| n-C₃H₇ | cyclohexene-F | phenyl | OCHF₂ | H | F |

-continued

| R | A | B | X | L¹ | L² |
|---|---|---|---|----|----|
| n-C₃H₇ | cyclohexene-F | phenyl | OCHF₂ | F | F |
| n-C₃H₇ | cyclohexene-F | phenyl-F | OCHF₂ | H | H |
| n-C₃H₇ | cyclohexene-F | phenyl-F | OCHF₂ | H | F |
| n-C₃H₇ | cyclohexene-F | phenyl-F | OCHF₂ | F | F |
| n-C₃H₇ | cyclohexene-F | phenyl-F,F | OCHF₂ | H | H |
| n-C₃H₇ | cyclohexene-F | phenyl-F,F | OCHF₂ | H | F |
| n-C₃H₇ | cyclohexene-F | phenyl-F,F | OCHF₂ | F | F |
| n-C₅H₁₁ | cyclohexene-F | phenyl | OCHF₂ | H | H |
| n-C₅H₁₁ | cyclohexene-F | phenyl | OCHF₂ | H | F |
| n-C₅H₁₁ | cyclohexene-F | phenyl | OCHF₂ | F | F |

-continued

| R | A | B | X | L¹ | L² |
|---|---|---|---|----|----|
| n-C₅H₁₁ | cyclohexene-F | phenyl-F | OCHF₂ | H | H |
| n-C₅H₁₁ | cyclohexene-F | phenyl-F | OCHF₂ | H | F |
| n-C₅H₁₁ | cyclohexene-F | phenyl-F | OCHF₂ | F | F |
| n-C₅H₁₁ | cyclohexene-F | phenyl-F,F | OCHF₂ | H | H |
| n-C₅H₁₁ | cyclohexene-F | phenyl-F,F | OCHF₂ | H | F |
| n-C₅H₁₁ | cyclohexene-F | phenyl-F,F | OCHF₂ | F | F |
| n-C₃H₇ | cyclohexene-F | phenyl | OCH₂CF₃ | H | H |
| n-C₃H₇ | cyclohexene-F | phenyl | OCH₂CF₃ | H | F |
| n-C₃H₇ | cyclohexene-F | phenyl | OCH₂CF₃ | F | F |

-continued

| R | A | B | X | L¹ | L² |
|---|---|---|---|----|----|
| n-C₃H₇ | cyclohexene-F | phenyl-F | OCH₂CF₃ | H | H |
| n-C₃H₇ | cyclohexene-F | phenyl-F | OCH₂CF₃ | H | F |
| n-C₃H₇ | cyclohexene-F | phenyl-F | OCH₂CF₃ | F | F |
| n-C₃H₇ | cyclohexene-F | phenyl-F,F | OCH₂CF₃ | H | H |
| n-C₃H₇ | cyclohexene-F | phenyl-F,F | OCH₂CF₃ | H | F |
| n-C₃H₇ | cyclohexene-F | phenyl-F,F | OCH₂CF₃ | F | F |
| n-C₅H₁₁ | cyclohexene-F | phenyl | OCH₂CF₃ | H | H |
| n-C₅H₁₁ | cyclohexene-F | phenyl | OCH₂CF₃ | H | F |
| n-C₅H₁₁ | cyclohexene-F | phenyl | OCH₂CF₃ | F | F |
| n-C₅H₁₁ | cyclohexene-F | phenyl-F | OCH₂CF₃ | H | H |

-continued

| R | A | B | X | L¹ | L² |
|---|---|---|---|----|----|
| n-C₅H₁₁ | cyclohexene-F | phenyl-F | OCH₂CF₃ | H | F |
| n-C₅H₁₁ | cyclohexene-F | phenyl-F | OCH₂CF₃ | F | F |
| n-C₅H₁₁ | cyclohexene-F | phenyl-F,F | OCH₂CF₃ | H | H |
| n-C₅H₁₁ | cyclohexene-F | phenyl-F,F | OCH₂CF₃ | H | F |
| n-C₅H₁₁ | cyclohexene-F | phenyl-F,F | OCH₂CF₃ | F | F |
| n-C₃H₇ | cyclohexene-F | phenyl | OCF₂CF₃ | H | H |
| n-C₃H₇ | cyclohexene-F | phenyl | OCF₂CF₃ | H | F |
| n-C₃H₇ | cyclohexene-F | phenyl | OCF₂CF₃ | F | F |
| n-C₃H₇ | cyclohexene-F | phenyl-F | OCF₂CF₃ | H | H |

-continued

| R | A | B | X | L¹ | L² |
|---|---|---|---|----|----|
| n-C₃H₇ | cyclohexene-F | phenyl-F | OCF₂CF₃ | H | F |
| n-C₃H₇ | cyclohexene-F | phenyl-F | OCF₂CF₃ | F | F |
| n-C₃H₇ | cyclohexene-F | phenyl-F,F | OCF₂CF₃ | H | H |
| n-C₃H₇ | cyclohexene-F | phenyl-F,F | OCF₂CF₃ | H | F |
| n-C₃H₇ | cyclohexene-F | phenyl-F,F | OCF₂CF₃ | F | F |
| n-C₅H₁₁ | cyclohexene-F | phenyl | OCF₂CF₂H | H | H |
| n-C₅H₁₁ | cyclohexene-F | phenyl | OCF₂CF₂H | H | F |
| n-C₅H₁₁ | cyclohexene-F | phenyl | OCF₂CF₂H | F | F |
| n-C₅H₁₁ | cyclohexene-F | phenyl-F | OCF₂CF₂H | H | H |
| n-C₅H₁₁ | cyclohexene-F | phenyl-F | OCF₂CF₂H | H | F |

-continued

| R | A | B | X | L¹ | L² |
|---|---|---|---|----|----|
| n-C₅H₁₁ | cyclohexene-F | phenyl-F | OCF₂CF₂H | F | F |
| n-C₅H₁₁ | cyclohexene-F | phenyl-F,F | OCF₂CF₂H | H | H |
| n-C₅H₁₁ | cyclohexene-F | phenyl-F,F | OCF₂CF₂H | H | F |
| n-C₅H₁₁ | cyclohexene-F | phenyl-F,F | OCF₂CF₂H | F | F |
| n-C₃H₇ | cyclohexene-F | phenyl-F | OCHFCF₃ | H | H |
| n-C₃H₇ | cyclohexene-F | phenyl-F | OCHFCF₃ | H | F |
| n-C₃H₇ | cyclohexene-F | phenyl-F | OCHFCF₃ | F | F |
| n-C₃H₇ | cyclohexene-F | phenyl-F,F | OCHFCF₃ | H | H |
| n-C₃H₇ | cyclohexene-F | phenyl-F,F | OCHFCF₃ | H | F |

-continued
| R | A | B | X | L¹ | L² |
|---|---|---|---|---|---|
| n-C₃H₇ | 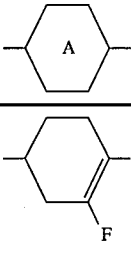 | 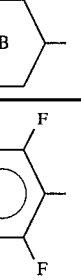 | OCHFCF₃ | F | F |
| n-C₅H₁₁ | 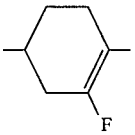 | 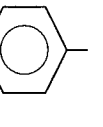 | OCH₂CF₂H | H | H |
| n-C₅H₁₁ | 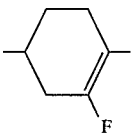 | 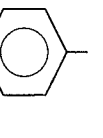 | OCH₂CF₂H | H | F |
| n-C₅H₁₁ | 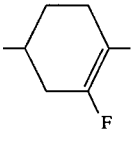 | 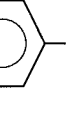 | OCH₂CF₂H | F | F |
| n-C₅H₁₁ | 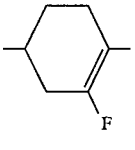 | 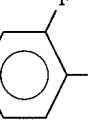 | OCH₂CF₂H | H | H |
| n-C₅H₁₁ | 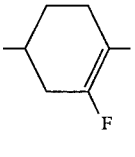 | 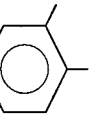 | OCH₂CF₂H | H | F |
| n-C₅H₁₁ | 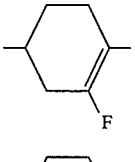 | 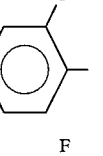 | OCH₂CF₂H | F | F |
| n-C₅H₁₁ | 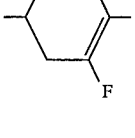 | 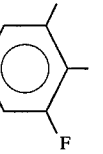 | OCH₂CF₂H | H | H |
| n-C₅H₁₁ | 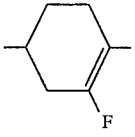 | 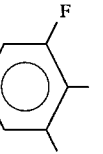 | OCH₂CF₂H | H | F |

-continued

| R | A | B | X | L¹ | L² |
|---|---|---|---|----|----|
| n-C₅H₁₁ | cyclohexene-F | phenyl-F,F | $OCH_2CF_2H$ | F | F |
| n-C₃H₇ | cyclohexene-F | phenyl | $OCH=CF_2$ | H | H |
| n-C₃H₇ | cyclohexene-F | phenyl | $OCH=CF_2$ | H | F |
| n-C₃H₇ | cyclohexene-F | phenyl | $OCH=CF_2$ | F | F |
| n-C₃H₇ | cyclohexene-F | phenyl-F | $OCH=CF_2$ | H | H |
| n-C₃H₇ | cyclohexene-F | phenyl-F | $OCH=CF_2$ | H | F |
| n-C₃H₇ | cyclohexene-F | phenyl-F | $OCH=CF_2$ | F | F |
| n-C₃H₇ | cyclohexene-F | phenyl-F,F | $OCH=CF_2$ | H | H |
| n-C₃H₇ | cyclohexene-F | phenyl-F,F | $OCH=CF_2$ | H | F |

-continued

| R | A | B | X | L¹ | L² |
|---|---|---|---|----|----|
| n-C₃H₇ | cyclohexene-F | phenyl-2,6-diF | OCH=CF₂ | F | F |
| n-C₅H₁₁ | cyclohexene-F | phenyl | OCH=CF₂ | H | H |
| n-C₅H₁₁ | cyclohexene-F | phenyl | OCH=CF₂ | H | F |
| n-C₅H₁₁ | cyclohexene-F | phenyl | OCH=CF₂ | F | F |
| n-C₅H₁₁ | cyclohexene-F | phenyl-2-F | OCH=CF₂ | H | H |
| n-C₅H₁₁ | cyclohexene-F | phenyl-2-F | OCH=CF₂ | H | F |
| n-C₅H₁₁ | cyclohexene-F | phenyl-2-F | OCH=CF₂ | F | F |
| n-C₅H₁₁ | cyclohexene-F | phenyl-2,6-diF | OCH=CF₂ | H | H |
| n-C₅H₁₁ | cyclohexene-F | phenyl-2,6-diF | OCH=CF₂ | H | F |

-continued

| R | A | B | X | L¹ | L² |
|---|---|---|---|---|---|
| n-C₅H₁₁ | cyclohexene-F | phenyl-F,F | $OCH=CF_2$ | F | F |
| n-C₃H₇ | cyclohexene-F | phenyl | $OCH=CF_2$ | H | H |
| n-C₃H₇ | cyclohexene-F | phenyl | $OCH=CF_2$ | H | F |
| n-C₃H₇ | cyclohexene-F | phenyl | $OCH=CF_2$ | F | F |
| n-C₃H₇ | cyclohexene-F | phenyl-F | $OCH=CF_2$ | H | H |
| n-C₃H₇ | cyclohexene-F | phenyl-F | $OCH=CF_2$ | H | F |
| n-C₃H₇ | cyclohexene-F | phenyl-F | $OCH=CF_2$ | F | F |
| n-C₃H₇ | cyclohexene-F | phenyl-F,F | $OCH=CF_2$ | H | H |
| n-C₃H₇ | cyclohexene-F | phenyl-F,F | $OCH=CF_2$ | H | F |

-continued

| R | A | B | X | L¹ | L² |
|---|---|---|---|----|----|
| n-C₃H₇ | cyclohexene-F | phenyl-2,6-diF | OCH=CF₂ | F | F |
| n-C₅H₁₁ | cyclohexene-F | phenyl | OCH=CF₂ | H | H |
| n-C₅H₁₁ | cyclohexene-F | phenyl | OCH=CF₂ | H | F |
| n-C₅H₁₁ | cyclohexene-F | phenyl | OCH=CF₂ | F | F |
| n-C₅H₁₁ | cyclohexene-F | phenyl-2-F | OCH=CF₂ | H | H |
| n-C₅H₁₁ | cyclohexene-F | phenyl-2-F | OCH=CF₂ | H | F |
| n-C₅H₁₁ | cyclohexene-F | phenyl-2-F | OCH=CF₂ | F | F |
| n-C₅H₁₁ | cyclohexene-F | phenyl-2,6-diF | OCH=CF₂ | H | H |
| n-C₅H₁₁ | cyclohexene-F | phenyl-2,6-diF | OCH=CF₂ | H | F |

-continued

| R | A | B | X | L¹ | L² |
|---|---|---|---|----|----|
| n-C₅H₁₁ | cyclohexene-F | phenyl-2F,6F | OCH=CF₂ | F | F |
| n-C₅H₁₁ | cyclohexene-F | phenyl | OCH₂C₂F₅ | H | H |
| n-C₅H₁₁ | cyclohexene-F | phenyl | OCH₂C₂F₅ | H | F |
| n-C₅H₁₁ | cyclohexene-F | phenyl | OCH₂C₂F₅ | F | F |
| n-C₅H₁₁ | cyclohexene-F | phenyl-2F | OCH₂C₂F₅ | H | H |
| n-C₅H₁₁ | cyclohexene-F | phenyl-2F | OCH₂C₂F₅ | H | F |
| n-C₅H₁₁ | cyclohexene-F | phenyl-2F | OCH₂C₂F₅ | F | F |
| n-C₅H₁₁ | cyclohexene-F | phenyl-2F,6F | OCH₂C₂F₅ | H | H |
| n-C₅H₁₁ | cyclohexene-F | phenyl-2F,6F | OCH₂C₂F₅ | H | F |

-continued

| R | A | B | X | L¹ | L² |
|---|---|---|---|----|----|
| n-C₅H₁₁ | cyclohexene-F | phenyl-F,F | OCH₂C₂F₅ | F | F |
| n-C₅H₁₁ | cyclohexene-F | phenyl | CN | H | H |
| n-C₅H₁₁ | cyclohexene-F | phenyl | CN | H | F |
| n-C₅H₁₁ | cyclohexene-F | phenyl | CN | F | F |
| n-C₅H₁₁ | cyclohexene-F | phenyl-F | CN | H | H |
| n-C₅H₁₁ | cyclohexene-F | phenyl-F | CN | H | F |
| n-C₅H₁₁ | cyclohexene-F | phenyl-F | CN | F | F |
| n-C₅H₁₁ | cyclohexene-F | phenyl-F,F | CN | H | H |
| n-C₅H₁₁ | cyclohexene-F | phenyl-F,F | CN | H | F |

-continued

| R | A | B | X | L¹ | L² |
|---|---|---|---|----|----|
| n-C₅H₁₁ | cyclohexene-F | phenyl-F,F | CN | F | F |
| n-C₃H₇ | cyclohexene-F | phenyl | C₂H₅ | H | H |
| n-C₃H₇ | cyclohexene-F | phenyl | C₂H₅ | H | F |
| n-C₃H₇ | cyclohexene-F | phenyl | C₂H₅ | F | F |
| n-C₃H₇ | cyclohexene-F | phenyl-F | C₂H₅ | H | H |
| n-C₃H₇ | cyclohexene-F | phenyl-F | C₂H₅ | H | F |
| n-C₃H₇ | cyclohexene-F | phenyl-F | C₂H₅ | F | F |
| n-C₃H₇ | cyclohexene-F | phenyl-F,F | C₂H₅ | H | H |
| n-C₃H₇ | cyclohexene-F | phenyl-F,F | C₂H₅ | H | F |

-continued

| R | A | B | X | L¹ | L² |
|---|---|---|---|----|----|
| n-C$_3$H$_7$ | cyclohexene-F | phenyl-2,6-diF | C$_2$H$_5$ | F | F |
| n-C$_5$H$_{11}$ | cyclohexene-F | phenyl | n-C$_3$H$_7$ | H | H |
| n-C$_5$H$_{11}$ | cyclohexene-F | phenyl | n-C$_3$H$_7$ | H | F |
| n-C$_5$H$_{11}$ | cyclohexene-F | phenyl | n-C$_3$H$_7$ | F | F |
| n-C$_5$H$_{11}$ | cyclohexene-F | phenyl-F | n-C$_3$H$_7$ | H | H |
| n-C$_5$H$_{11}$ | cyclohexene-F | phenyl-F | n-C$_3$H$_7$ | H | F |
| n-C$_5$H$_{11}$ | cyclohexene-F | phenyl-F | n-C$_3$H$_7$ | F | F |
| n-C$_5$H$_{11}$ | cyclohexene-F | phenyl-2,6-diF | n-C$_3$H$_7$ | H | H |
| n-C$_5$H$_{11}$ | cyclohexene-F | phenyl-2,6-diF | n-C$_3$H$_7$ | H | F |

-continued

| R | A | B | X | L¹ | L² |
|---|---|---|---|----|----|
| n-C₅H₁₁ | cyclohexene-F | phenyl-F,F | n-C₃H₇ | F | F |
| n-C₃H₇ | cyclohexene-F | phenyl | OCH₃ | H | H |
| n-C₃H₇ | cyclohexene-F | phenyl | OCH₃ | H | F |
| n-C₃H₇ | cyclohexene-F | phenyl | OCH₃ | F | F |
| n-C₃H₇ | cyclohexene-F | phenyl-F,F | OCH₃ | H | H |
| n-C₃H₇ | cyclohexene-F | phenyl-F | OCH₃ | H | F |
| n-C₃H₇ | cyclohexene-F | phenyl-F | OCH₃ | F | F |
| n-C₃H₇ | cyclohexene-F | phenyl-F,F | OCH₃ | H | H |
| n-C₃H₇ | cyclohexene-F | phenyl-F,F | OCH₃ | H | F |

-continued

| R | A | B | X | L¹ | L² |
|---|---|---|---|---|---|
| n-C₃H₇ | cyclohexene-F | phenyl-F,F | OCH₃ | F | F |
| n-C₅H₁₁ | cyclohexene-F | phenyl | OC₂H₅ | H | H |
| n-C₅H₁₁ | cyclohexene-F | phenyl | OC₂H₅ | H | F |
| n-C₅H₁₁ | cyclohexene-F | phenyl | OC₂H₅ | F | F |
| n-C₅H₁₁ | cyclohexene-F | phenyl-F | OC₂H₅ | H | H |
| n-C₅H₁₁ | cyclohexene-F | phenyl-F | OC₂H₅ | H | F |
| n-C₅H₁₁ | cyclohexene-F | phenyl-F | OC₂H₅ | F | F |
| n-C₅H₁₁ | cyclohexene-F | phenyl-F,F | OC₂H₅ | H | H |
| n-C₅H₁₁ | cyclohexene-F | phenyl-F,F | OC₂H₅ | H | F |

-continued

| R | A | B | X | L¹ | L² | |
|---|---|---|---|----|----|---|
| n-C₅H₁₁ | cyclohexene-F | difluorophenyl | OC₂H₅ | F | F | |
| n-C₃H₇ | cyclohexene-F | cyclohexyl | F | H | H | |
| n-C₃H₇ | cyclohexene-F | cyclohexyl | F | H | F | $T_{(N,I)} = 95°$ C.; $\Delta\epsilon = 8.0$; $\Delta n = +0.093$ |
| n-C₃H₇ | cyclohexene-F | cyclohexyl | F | F | F | |
| n-C₅H₁₁ | cyclohexene-F | cyclohexyl | OCF₃ | H | H | |
| n-C₅H₁₁ | cyclohexene-F | cyclohexyl | OCF₃ | H | F | |
| n-C₅H₁₁ | cyclohexene-F | cyclohexyl | OCF₃ | F | F | |

EXAMPLE 2

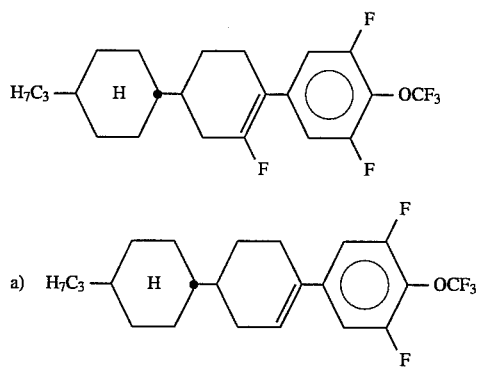

Two drops of bromine are added to a suspension of 0.25 mol of magnesium turnings in 60 ml of ether. A solution of 0.2 mol of 3,5-difluoro-4-trifluoromethoxybromobenzene in 60 ml of ether is subsequently added dropwise. The mixture is stirred for a further 0.5 hour, and a solution of 0.2 mol of 4-trans-4-propylcyclohexylcyclohexanone in 50 ml of ether is then added dropwise at 20°–25° C. to the Grignard reagent. The mixture is stirred for a further 2 hours, poured into 500 ml of water, acidified and extracted by shaking with ether. The organic phase is evaporated to dryness. The residue is dissolved in toluene and refluxed for 5 hours with p-toluenesulfonic acid on a water separator. The mixture is subsequently cooled to room temperature, neutralized and is subjected to customary work-up.

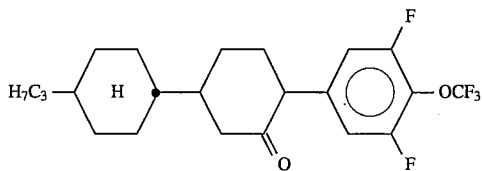

0.2 mol of the cyclohexene derivative from Example 1a) are dissolved in 200 ml of THF, and 0.2 g of sodium borohydride is added. 0.24 mol of $BF_3$ etherate are added dropwise to the mixture, during which the temperature of the reaction mixture should not exceed 10° C. The mixture is subsequently stirred at room temperature for a further 2 hours. After hydrolysis, the reaction mixture is treated directly, without further work-up, with a sulfuric acid solution of sodium dichromate. During the oxidation, the reaction temperature should not be higher than 15° C. The mixture is stirred for a further 1 hour at room temperature and for a further 0.5 hour at 30° C. The mixture is filtered, the filtrate is extracted with ether, the extract is washed with water, and the solvent is removed in vacuo. The residue is purified by chromatography.

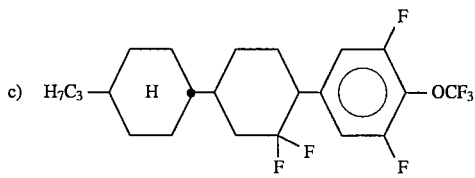

0.01 mol of the ketone from b) are treated with 0.025 mol of diethylaminosulfur trifluoride at 60° C. for 15 hours. The mixture is then introduced dropwise into ice water with stirring. After the addition of ether, the organic phase is separated off and subjected to customary work-up.

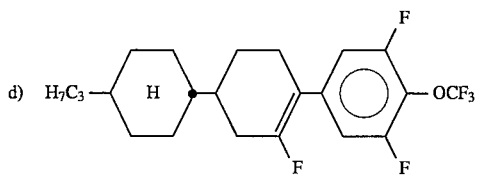

13.5 mol of diisopropylamine are added dropwise at −20° C. to 13.5 mol of BuLi (15% in n-hexane) in 10 ml of THF. The solution is subsequently stirred for 10 minutes and added dropwise at −40° C. under a protective gas to a mixture comprising 10 ml of THF and 13.5 mol of the geminal difluoro compound from c).

The mixture is stirred for 0.5 hour firstly at −40° C. and subsequently overnight at room temperature. After hydrolysis, the product is subjected to customary work-up.

We claim:

1. A 2-Fluorocyclohexene compound of the formula I

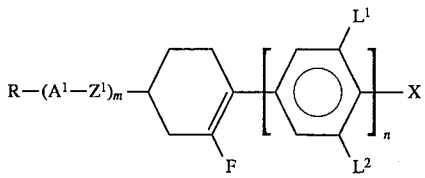

where

R is an alkyl or alkenyl radical having 1 to 18 carbon atoms which is unsubstituted or substituted by CN or by at least one halogen and in which one or more non-adjacent $CH_2$ groups can be replaced by a radical selected from the group consisting of —O—, —S—, —CO—, —O—CO—, —CO—O— and —C≡C—, $A^1$ a) is a 1,4-phenylene radical, in which one or two CH groups can be replaced by N, b) is a 1,4-cyclohexylene radical, in which one or two non-adjacent $CH_2$ groups can be replaced by —O— or —S—, c) is a 1,4-cyclohexenylene, piperidine-1,4-diyl, 1,4-bicyclo[2.2.2]octylene or naphthalene-2,6-diyl radical, where the radicals a) and b) can be monosubstituted or polysubstituted by halogen atoms or cyano and/or methyl groups, $Z^1$ is —$CH_2CH_2$—, —CO—O—, —O—CO—, —CH=CH—, —$OCH_2$—, —$CH_2O$—, —C≡C—, —$(CH_2)_4$—, —CH=CH—$CH_2CH_2$— or a single bond, X is alkyl or alkoxy having 1 to 12 carbon atoms, NCS or Q—Y, where Q is —O—, —S— or a single bond, and Y is CN, F, Cl or halogenated alkyl or alkenyl having 1 to 5 carbon atoms, $L^1$ and $L^2$ are each, independently of one another, H or F, m is 0, 1 or 2, and n is 1 or 2.

2. A 2-fluorocyclohexene compound of claim 1 of the formula

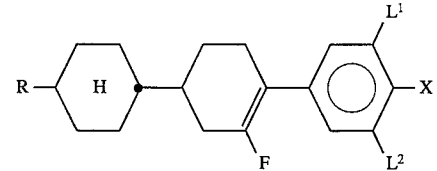

in which R, X, $L^1$ and $L^2$ are as defined in claim 1.

3. A 2-fluorocyclohexene compound of claim 1 of the formula

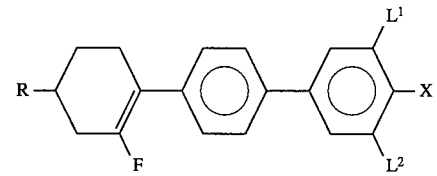

in which R, X, $L^1$ and $L^2$ are as defined in claim 1.

4. A 2-fluorocyclohexene compound of claim 1 of the formula

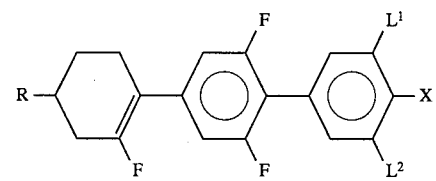

in which R, X, $L^1$ and $L^2$ are as defined in claim 1.

5. A compound of the formula I of claim 1 in which $L^1$ and $L^2$ are fluorine.

6. A compound of the formula I of claim 1 in which X is CN, F, Cl, $OCF_3$, $OCHF_2$, $CF_3$, $OCHFCF_3$, $OCH_2CF_3$, OCH=$CF_2$ or OCF=$CF_2$.

7. A compound of the formula I of claim 1 in which m+n=2.

8. A fluid-crystalline medium having at least two components, wherein at least one component is a compound of the formula I of claim 1.

9. An electro-optical display element, comprising, as dielectric, a liquid-crystalline medium according to claim 8.

10. A matrix liquid-crystalline display element comprising, as dielectric, a liquid-crystalline medium according to claim 8.

11. A compound according to claim 1, wherein $A^1$ is 1,4-cyclohexylene optionally mono- or di-substituted by F or CN, 1,4-cyclohexenylene 1,3-dioxane-2,5-diyl, 1,3-dithiane-2,5-diyl, 1,4-phenylene optionally mono- or di-substituted by F or CN, pyridine-2,5-diyl or bicyclo(2,2,2)octylene.

12. A compound according to claim 1, wherein $A^1$ is 1,4-cyclohexylene or 1,4-phenylene.

* * * * *